United States Patent
Fisher et al.

(10) Patent No.: US 11,660,100 B2
(45) Date of Patent: May 30, 2023

(54) RADIALLY EXPANDING DEBRIDEMENT TOOLS

(71) Applicant: DSM IP Assets B.V., Heerlen (NL)

(72) Inventors: William T. Fisher, Exton, PA (US);
Timothy Ringeisen, Exton, PA (US);
Gino Bradica, Exton, PA (US)

(73) Assignee: DSM IP ASSETS B.V., Heerlen (NL)

( * ) Notice: Subject to any disclaimer, the term of this patent is extended or adjusted under 35 U.S.C. 154(b) by 234 days.

(21) Appl. No.: 16/962,464

(22) PCT Filed: Jan. 25, 2019

(86) PCT No.: PCT/US2019/015113
§ 371 (c)(1),
(2) Date: Jul. 15, 2020

(87) PCT Pub. No.: WO2019/164634
PCT Pub. Date: Aug. 29, 2019

(65) Prior Publication Data
US 2021/0077123 A1    Mar. 18, 2021

Related U.S. Application Data

(60) Provisional application No. 62/622,273, filed on Jan. 26, 2018.

(30) Foreign Application Priority Data

Mar. 16, 2018   (EP) ..................................... 18162425

(51) Int. Cl.
*A61B 17/16* (2006.01)
*A61B 17/00* (2006.01)

(52) U.S. Cl.
CPC ........ *A61B 17/1615* (2013.01); *A61B 17/164* (2013.01); *A61B 17/1633* (2013.01); *A61B 17/1659* (2013.01); *A61B 2017/00867* (2013.01)

(58) Field of Classification Search
CPC . A61B 17/16; A61B 17/1615; A61B 17/1622; A61B 17/1624; A61B 17/1626;
(Continued)

(56) References Cited

U.S. PATENT DOCUMENTS 5,245,987 A * 9/1993 Redmond .......... A61B 17/0218
600/206
5,885,258 A * 3/1999 Sachdeva ........... A61B 1/00082
606/198

(Continued)

FOREIGN PATENT DOCUMENTS

WO   WO2004107955 A2   12/2004
WO   WO2010121172 A1   10/2010
(Continued)

*Primary Examiner* — Eric S Gibson
(74) *Attorney, Agent, or Firm* — Kevin M. Bull

(57) ABSTRACT

Disclosed are radially expanding debridement tools configured to pass through an access channel present in a first tissue of a living being, expand radially, and create a void in a second tissue of the living being upon being advanced distally through the access channel and into the second tissue while being rotated, wherein the shape of the void comprises at least one step. Further disclosed are debridement systems and methods of treating tissue defects in living beings.

17 Claims, 8 Drawing Sheets

(58) Field of Classification Search
CPC ............ A61B 17/1628; A61B 17/1631; A61B 17/1633; A61B 17/164; A61B 17/1655; A61B 17/1657; A61B 17/1659
See application file for complete search history.

(56) References Cited

U.S. PATENT DOCUMENTS

| | | | | |
|---|---|---|---|---|
| 6,440,138 | B1* | 8/2002 | Reiley | A61B 17/1671 606/45 |
| 6,863,672 | B2* | 3/2005 | Reiley | A61B 17/320016 606/79 |
| 7,641,664 | B2* | 1/2010 | Pagano | A61B 17/8858 606/92 |
| 8,034,088 | B2* | 10/2011 | Pagano | A61B 17/8858 606/279 |
| 8,961,518 | B2* | 2/2015 | Taylor | A61B 17/1637 606/86 R |
| 9,084,615 | B2* | 7/2015 | Cleveland | A61B 17/1659 |
| 9,381,031 | B2* | 7/2016 | Rains | A61B 17/164 |
| 9,848,889 | B2* | 12/2017 | Taylor | A61B 17/1671 |
| 11,219,466 | B2* | 1/2022 | Seykora | A61B 17/1622 |
| 2002/0013600 | A1 | 1/2002 | Scribner | |
| 2002/0183758 | A1 | 12/2002 | Middleton | |
| 2002/0188299 | A1 | 12/2002 | Reiley | |
| 2004/0024410 | A1 | 2/2004 | Olson, Jr. et al. | |
| 2007/0060933 | A1* | 3/2007 | Sankaran | A61B 17/3207 606/160 |
| 2014/0214042 | A1* | 7/2014 | Cleveland | A61B 17/1659 606/83 |
| 2014/0276840 | A1 | 9/2014 | Richter | |
| 2015/0164514 | A1 | 6/2015 | Wlodarski | |
| 2021/0077123 | A1* | 3/2021 | Fisher | A61F 2/28 |

FOREIGN PATENT DOCUMENTS

| | | | | |
|---|---|---|---|---|
| WO | WO-2011011664 A2 * | 1/2011 | ......... | A61B 17/1617 |
| WO | WO-2011091052 A1 * | 7/2011 | ......... | A61B 17/1604 |
| WO | WO2011091052 A1 | 7/2011 | | |
| WO | WO2015057195 A1 | 4/2015 | | |
| WO | WO-2019164634 A1 * | 8/2019 | ......... | A61B 17/0401 |

* cited by examiner

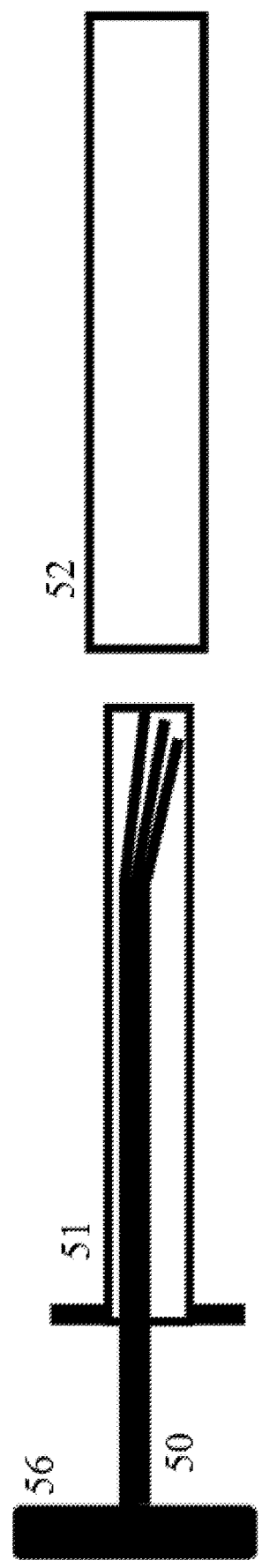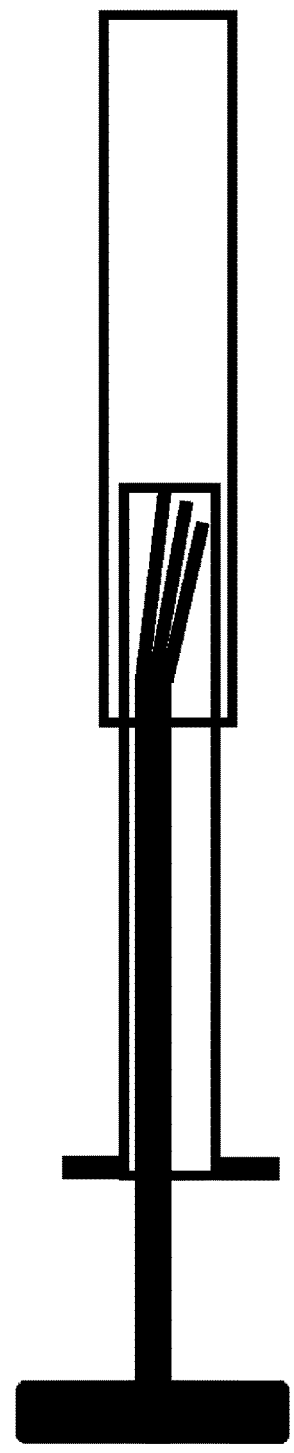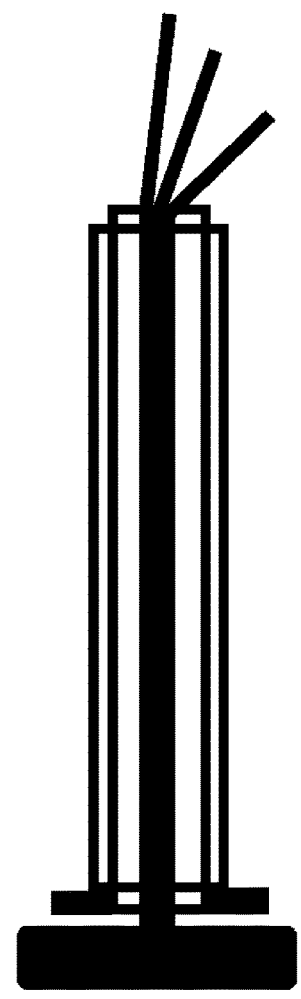

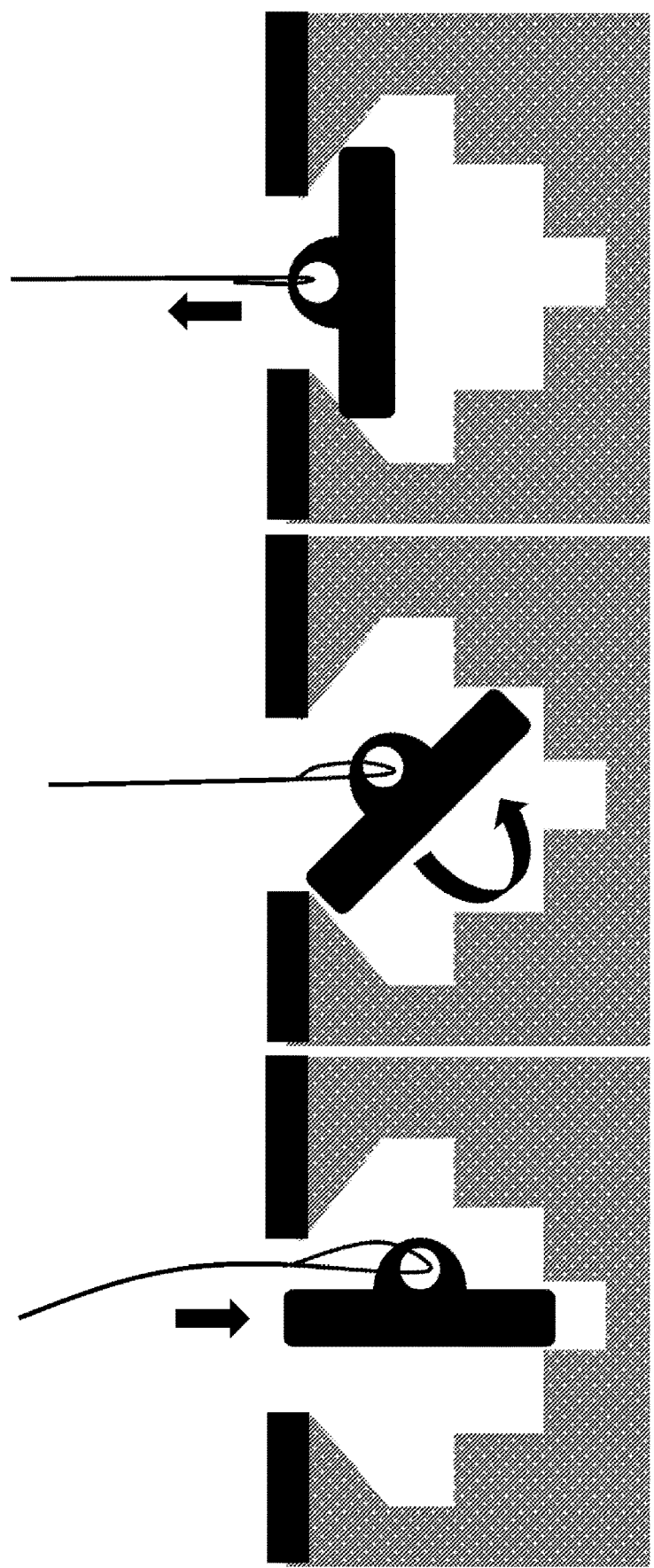

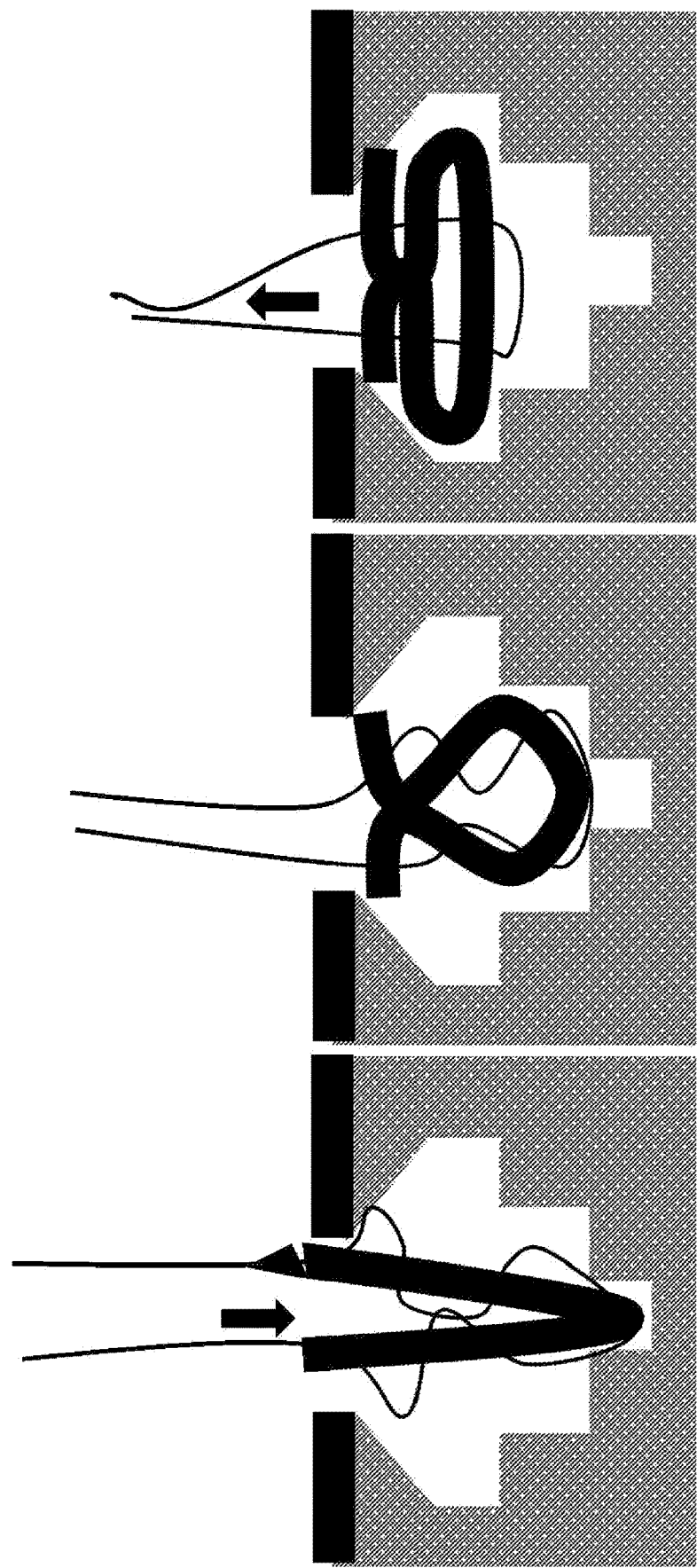

RADIALLY EXPANDING DEBRIDEMENT TOOLS

CROSS-REFERENCE TO RELATED APPLICATIONS

This application is a U.S. national phase entry under 35 USC 371 of international application PCT/US2019/015113, filed 25 Jan. 2019, which designated the U.S. and claims priority to U.S. Provisional Application 62/622,273, filed 26 Jan. 2018, and European Patent Application EP18162425.5, filed 16 Mar. 2018, the entire contents of each of which are hereby incorporated by reference in their entirety.

FIELD

The present inventions relate to surgical debridement tools capable of forming a void in a tissue through an access channel and methods of forming, and optionally filling, a void in a tissue.

BACKGROUND

Avascular necrosis, also known as bone necrosis, osteonecrosis, aseptic necrosis, and ischemic bone necrosis, is a common disease characterized by progressive tissue damage leading to death of cellular elements of bone and/or marrow. Avascular necrosis most commonly occurs in the shoulder and hip, but also occurs frequently in bones of the spine, knees, foot, ankle, and jaw.

The appearance of bone marrow lesions is indicative of avascular necrosis. There are 4 bone marrow lesion stages of avascular necrosis that correspond to the severity of the bone damage. Various approaches have been employed for treating the different bone marrow lesion stages of avascular necrosis. Untreated, avascular necrosis worsens with time. Eventually the bone becomes so weakened that it collapses.

There are numerous treatment options for avascular necrosis. Non-operative treatments include rest, non-weight-bearing exercises, protected weight-bearing, pharmacotherapy (e.g., non-steroidal anti-inflammatory drugs and bisphosphonate medications such as alendronate or risedronate), and electrical stimulation. Should non-operative treatment fail, allowing the condition to become chronic, operative treatments include fusion, osteotomy, hemi-resurfacing, hemi-arthroplasty, debridement and grafting, core decompression with or without grafting, as well as total joint arthroplasty.

Many surgeons consider core decompression medically necessary for the treatment of early/pre-collapse (stage I or II; before X-ray changes are evident) avascular necrosis, in an effort to avoid more invasive and expensive operative treatments. Unfortunately, current core decompression procedures using drill bits to reach and remove the bone lesion are limited in diameter so as to not compromise the integrity of the surrounding cortical bone, thus they do not adequately treat the volume of the bone lesion, leaving a majority of the compromised bone tissue undisrupted.

A commercially available debridement tool for core decompression is the X-REAM™ Percutaneous Expandable Reamer distributed by Wright Medical, for treatment of deep bone marrow lesions of the femoral head. Commercially available systems are expensive, dependent upon expanding an already large pilot hole, and are difficult to shrink down in size to provide therapy to bones associated with smaller joints.

WO2011/091052 discloses an apparatus and methods for bone access and cavity preparation. The apparatus comprises a broaching member that may be expandable inside the bone. A broaching member may be flexible such that it allegedly broaches bone having a relatively lower density and it leaves bone having a relatively higher density substantially intact.

Further examples of expanding debridement tools are described in US2002/0188299 and US2002/0013600.

A typical procedure for treating avascular necrosis using an expanding debridement tool proceeds as follows. First, a narrow access channel is created in a first tissue, for instance cortical tissue. The access channel may be created by, for example, a drill bit or a trocar. Optionally, a cannula or guide tube may be inserted in the access channel. Next, the expanding debridement tool is inserted in the access channel and advanced distally through the first tissue and into the second tissue, for instance cancellous bone. The expanding debridement tool may be contained within a carrier tube, in which case the carrier tube is inserted in the access channel and advanced distally through the first tissue and into the second tissue. Upon reaching the desired location, the expanding debridement tool is advanced beyond the guide tube, cannula, or carrier tube and further into the second tissue. The expanding debridement tool is then expanded, creating a void. The now expanded debridement tool is then rotated to enlarge the void. The proximal end of the expanding debridement tool may be connected to a drill to facilitate rotation or may contain a knob to facilitate rotation by hand. Subsequently, the debridement tool and carrier tube, if present, are withdrawn from the tissue. Optionally, the void is then aspirated and/or a support matrix is placed in the void.

SUMMARY

Whereas the prior art debridement tools create a void in the shape of a single ellipsoid in a target tissue, the radially expanding debridement tools disclosed herein create a void comprising at least one step from a first void section to a second void section, wherein the first void section is more distal than the second void section, and wherein the first void section comprises a maximum radial cross-sectional area that is less than the maximum radial cross-sectional area of the second void section. In an embodiment, a radially expanding debridement tool is configured to pass through an access channel present in a first tissue of a living being, expand radially, and create a void in a second tissue of the living being upon being advanced distally through the access channel and into the second tissue while being rotated, wherein the shape of the void comprises at least one step from a first void section to a second void section, wherein the first void section is more distal than the second void section, and wherein the first void section comprises a maximum radial cross-sectional area that is less than the maximum radial cross-sectional area of the second void section.

Voids comprising at least one step may provide several benefits over a single ellipsoid-shaped void. Stepwise tissue disruption may reduce the overall amount of target tissue needed to be disrupted when the support matrix is a suture anchor, such as a tilting or expanding suture anchor. In this way, the anchor can be inserted deep into the narrowest step of the void prior to being expanded or tilted, and then pulled up tight into the widest of the void steps. This process may have the additional benefit of reducing pressure tissue necrosis that is often seen in expanding all-suture anchors. In the case of a support matrix that does not completely fill the bone void, the remainder can be left open to fill with blood from the surrounding tissue or filled with a second support matrix. In an embodiment, the support matrix is an autograft, allograft, xenograft, synthetic bone graft, suture mass, suture anchor, screw, or tissue marker.

Further disclosed embodiments of the invention include debridement systems and methods of treating a tissue defect in a living being.

BRIEF DESCRIPTION OF THE DRAWINGS

FIG. 5 is a schematic of an embodiment of a debridement system comprising a radially expanding debridement tool and a carrier tube.

FIG. 6 depicts the placement of a solid suture anchor in a void formed by a radially expanding debridement tool.

FIG. 7 depicts the placement of a flexible or expanding suture anchor in the void formed by a radially expanding debridement tool.

DETAILED DESCRIPTION

In an embodiment, a radially expanding debridement tool is configured to pass through an access channel present in a first tissue of a living being, expand radially, and create a void in a second tissue of the living being upon being advanced distally through the access channel and into the second tissue while being rotated, wherein the shape of the void comprises at least one step.

Such tissue debridement tools are typically useful in treating tissue defects associated with non-cortical tissue. The non-cortical tissue is typically adjacent to a joint or associated with a joint, such as associated with the hip, knee, elbow, foot, ankle, mandible, or shoulder, or may be associated with soft tissue such as the breast or annulus. In an embodiment, the first tissue is cortical tissue. In an embodiment, the first tissue is cortical bone and the second tissue is cancellous bone.

A void is defined as the volume of tissue greater than the width of the access channel that would be disrupted by the debridement tool that is rotated while advancing the debridement tool distally into the second tissue. A drill bit that is advanced through cortical tissue and into a second tissue does not create a void because the volume of tissue that is disrupted is not greater than the width of the access channel.

The radially expanding debridement tool is configured to create a void that comprises at least one step. A step is characterized by a discontinuity in width between a first location of a void and second location of a void. For example, a void having the shape of two cylinders of different diameters stacked on one another possess a step because there is a discontinuity in width at the interface of the two cylinders. A single ellipsoid-shaped void does not comprise a step.

In an embodiment, the void comprises at least two steps. In an embodiment, the void comprises from two to five steps. In an embodiment, the void comprises at least two steps of varying diameter. In an embodiment, the void comprises from two to five steps of varying diameter.

Figure 1A:
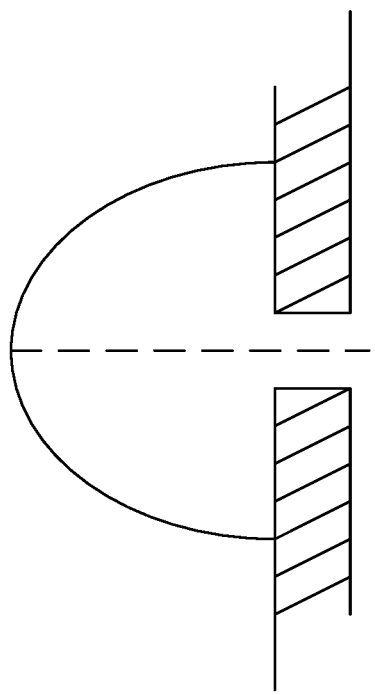
FIG. 1A-1C depict single ellipsoid voids that do not comprise a step.
Figure 1B:
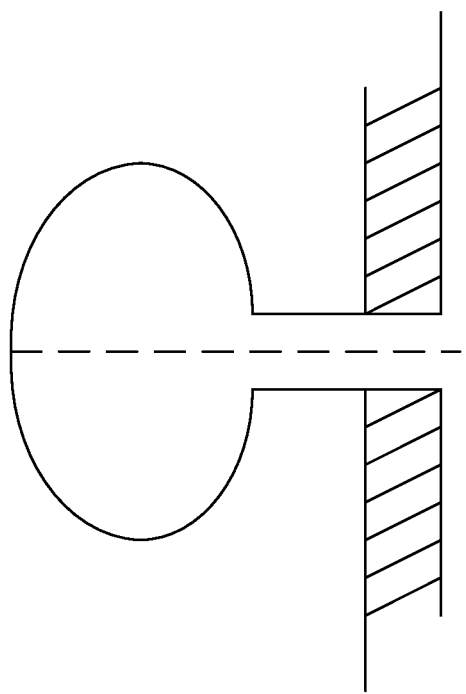
Figure 1C:
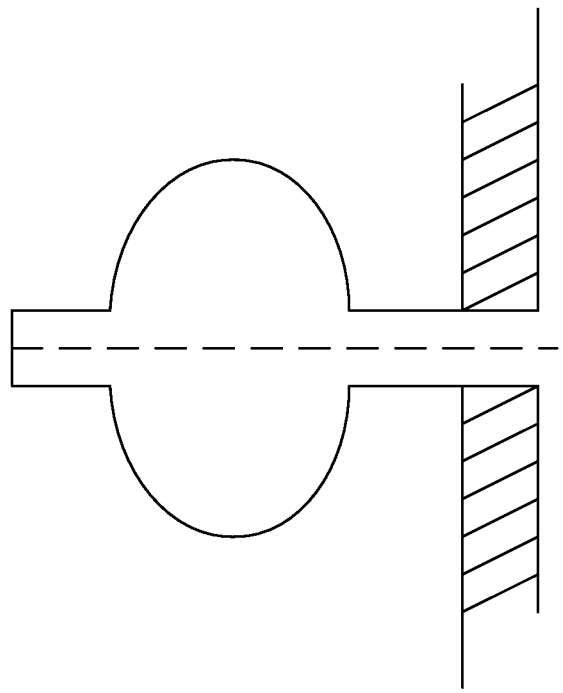
Figure 2A:
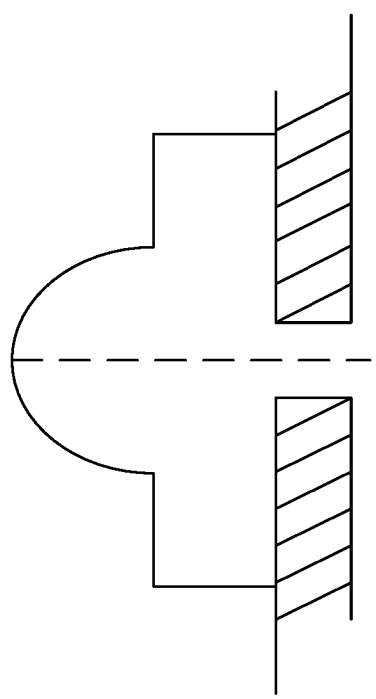
FIG. 2A-2E depict voids that comprise at least one step.
Figure 2B:
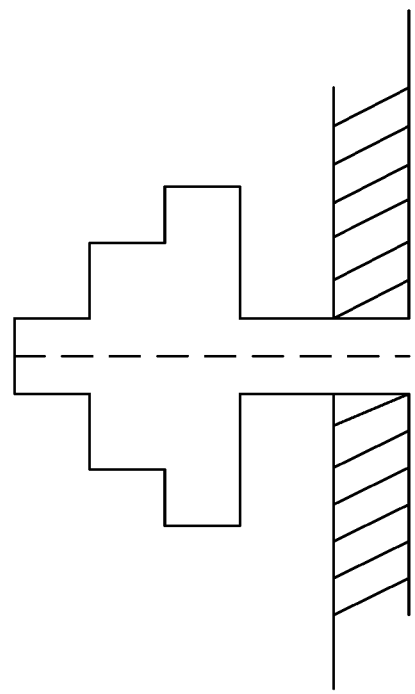
Figure 2C:
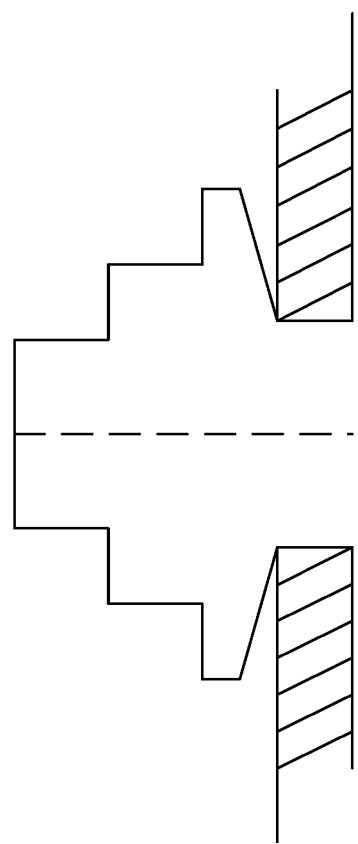
Figure 2D:
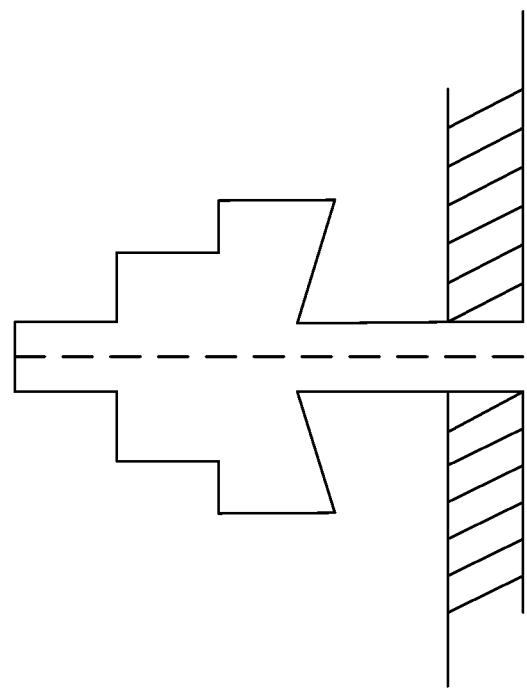
Figure 2E:
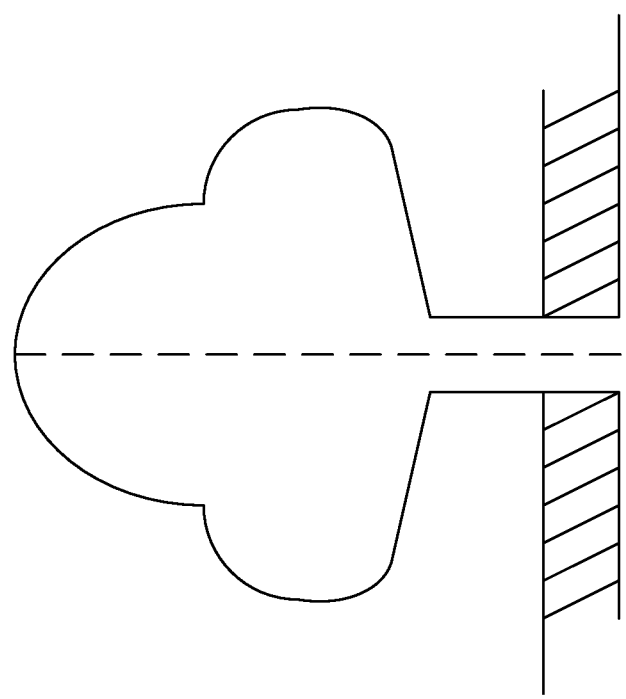

Voids that do not comprise at least one step are shown in FIGS. 1A-1C. Voids that comprise at least one step are depicted in FIGS. 2A-2E. In an embodiment, the void comprises a taper from the access channel to the void's maximum width, as pictured in FIG. 2C-2E.

In an embodiment, the void comprises at least one step from a first void section to a second void section. In other words, the step marks the location where the first void section ends and where the second void section begins. A void comprises one more void section than the void comprises steps.

Throughout this application, a void section with a lower number, e.g. first, is more distal than a void section with a higher number, e.g. third. In an embodiment, a first void section is the portion of the void that is present from the void's most distal point to the first step. In an embodiment of a void comprising two steps, the first void section is the portion of the void that is present from the void's most distal point to the more distal step, the second void section is the portion of the void from the first step to the more proximal step, and the third void section is the remainder of the void.

In an embodiment, the first void section comprises a maximum radial cross-sectional area that is less than the maximum radial cross-sectional area of the second void section, wherein the first void section is more distal than the second void section. The maximum radial cross-sectional area for a given void section is the largest area of the void section in any of the planes that are perpendicular to the axis of rotation of the radially expanding debridement tool after one full rotation of the radially expanding debridement tool.

In an embodiment, the void comprises at least one step, at least two steps, or at least three steps. In an embodiment, the void comprises at least two void sections, at least three void sections, or at least four void sections.

In an embodiment, the void section with the greatest maximum radial cross-sectional area is the most proximal void section. In an embodiment, the void section with the smallest maximum radial cross-sectional area is the most distal void section.

In an embodiment, a second void section has a maximum radial cross-sectional area that is at least 1.05 times, at least 1.1 times, at least 1.2 times, at least 1.3 times, at least 1.4 times, at least 1.5 times, at least 1.6 times, at least 1.7 times, at least 1.8 times, at least 1.9 times, at least 2 times, at least 2.1 times, at least 2.2 times, at least 2.3 times, at least 2.4 times, or at least 2.5 times the maximum radial cross-sectional area of a first void section, wherein the first void section is more distal than the second void section. In an embodiment, a second void section has a maximum radial cross-sectional area that is at most 10 times, at most 9 times, at most 8 times, at most 7 times, at most 6 times, at most 5 times, at most 4 times, at most 3 times, at most 2.5 times, at most 2 times, or at most 1.5 times the maximum radial cross-sectional area of a first void section, wherein the first void section is more distal than the second void section.

In an embodiment, a third void section has a maximum radial cross-sectional area that is at least 1.05 times, at least 1.1 times, at least 1.2 times, at least 1.3 times, at least 1.4 times, at least 1.5 times, at least 1.6 times, at least 1.7 times, at least 1.8 times, at least 1.9 times, at least 2 times, at least 2.1 times, at least 2.2 times, at least 2.3 times, at least 2.4 times, or at least 2.5 times the maximum radial cross-sectional area of a second void section, wherein the second void section is more distal than the third void section. In an embodiment, a third void section has a maximum radial cross-sectional area that is at most 10 times, at most 9 times, at most 8 times, at most 7 times, at most 6 times, at most 5 times, at most 4 times, at most 3 times, at most 2.5 times, at most 2 times, or at most 1.5 times the maximum radial cross-sectional area of a second void section, wherein the second void section is more distal than the third void section.

In an embodiment, a fourth void section has a maximum radial cross-sectional area that is at least 1.05 times, at least 1.1 times, at least 1.2 times, at least 1.3 times, at least 1.4 times, at least 1.5 times, at least 1.6 times, at least 1.7 times, at least 1.8 times, at least 1.9 times, at least 2 times, at least 2.1 times, at least 2.2 times, at least 2.3 times, at least 2.4 times, or at least 2.5 times the maximum radial cross-sectional area of a third void section, wherein the third void section is more distal than the fourth void section. In an embodiment, a fourth void section has a maximum radial cross-sectional area that is at most 10 times, at most 9 times, at most 8 times, at most 7 times, at most 6 times, at most 5 times, at most 4 times, at most 3 times, at most 2.5 times, at most 2 times, or at most 1.5 times the maximum radial cross-sectional area of a third void section, wherein the third void section is more distal than the fourth void section.

In an embodiment, the void comprises a minimum width at the most distal end of the void and a greater width at the portion of the void that is nearest the access channel. In an embodiment, the void comprises the shape of a plurality of concentric cylinders abutting one another. In an embodiment, the void comprises the shape of at least two cylinders of different diameters, wherein a surface of a first cylinder of the at least two cylinders abuts the surface of a second cylinder of the at least two cylinders. In an embodiment, the at least two cylinders are coaxial. In an embodiment, the at least two cylinders are not coaxial. In an embodiment, the void comprises the shape of at least three cylinders of different diameters, wherein a surface of a first cylinder of the at least three cylinders abuts the surface of a second cylinder of the at least three cylinders.

Figure 3:
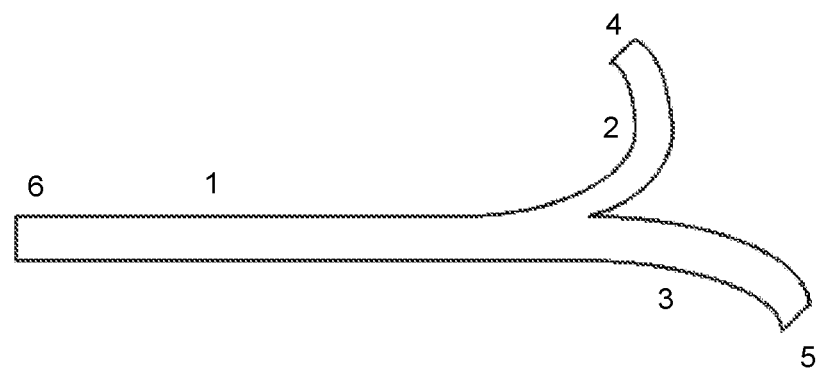
FIG. 3 depicts an embodiment of a radially expanding debridement tool.

FIG. 3 depicts a radially expanding debridement tool comprising a shaft 1 and two cutting wires 2, 3 extending from the shaft 1, the two cutting wires comprising a cutting edge and a tip 4, 5. The radially expanding debridement tool tips may expand or tilt radially due to at least one hinge connection or being formed of a material comprising shape memory. In an embodiment, at least one of the cutting wires comprises shape memory. In an embodiment, at least two cutting wires comprise shape memory. In an embodiment, one or more of the cutting wires comprise a plurality of tips. In an embodiment, the radially expanding debridement tool comprises two, three, four, or five cutting wires.

In an embodiment, the shaft is flexible. In an embodiment, the shaft is rigid. In an embodiment, the shaft is made from the same material as the cutting wires. In an embodiment, the shaft is made from a different material than the cutting wires. In an embodiment, the shaft has a circular cross-section. In an embodiment, the shaft has a polygonal cross-section. In an embodiment, the shaft comprises at least two cutting wires bonded or twisted together. In an embodiment, the shaft comprises a tube wherein the at least two cutting wires are crimped within the tube. The shaft may be engaged at its proximal end 6 by an operator in order to rotate the radially expanding debridement tool. The proximal end may comprise a knob or handle for easier turning by hand, or an interface to connect with a drill.

As pictured in FIG. 3, the tips of the cutting wires each possess a cutting edge. The number of cutting edges is typically dictated by the cross-section of the cutting wires. A wire with a square cross-section will typically include four cutting edges on its tips. If the cutting wire is smoothed or rounded at the tip, the tip may have no cutting edges. In an embodiment, the radially expanding debridement tool has a polygonal cross-section. In an embodiment, the radially expanding debridement tool has a triangular cross-section. In an embodiment, the radially expanding debridement tool has a square cross-section. In an embodiment, the radially expanding debridement tool has a rectangular cross-section. In an embodiment, the radially expanding debridement tool has a circular cross-section.

In an embodiment, the portion of each cutting wire that will enter the body is attached as a single unit to the portion of the each cutting wire that will remain outside the body. In other words, the cutting wires also form at least part of the shaft. This construction has the advantage that it reduces the likelihood of any part of the radially expanding debridement tool breaking off inside the body.

This type of construction can be accomplished in numerous ways. In an embodiment, the cutting wires are first given a preformed curvature. Next, the cutting wires may be placed inside a crimp tube and crimped such that a portion of the cutting wires is constrained and another portion is unconstrained. Other potential options are to weld the two cutting wires together, thereby creating a constrained and unconstrained portion, or to crimp (e.g. in a crimp tube) and then weld. In an embodiment, the radially expanding debridement tool is formed by twisting together two or more cutting wires into a single unit and then imparting a desired curvature to each individual cutting wire.

In an embodiment, a cutting wire has a cutting edge on at least a portion of its length. The length of a cutting wire is the portion of the cutting wire between its origin point along the shaft and its tip. In an embodiment, at least two cutting wires comprise a cutting edge along at least a portion of its length. In an embodiment, a cutting wire comprises a cutting edge along its entire length. In an embodiment, at least two cutting wires comprise a cutting edge along its entire length.

In an embodiment, at least two cutting wires comprise shape memory. The feature of shape memory allows each cutting wire to be constrained, e.g. in an access channel in cortical tissue or a carrier tube, and then, upon leaving the channel or tube spring out automatically into an expanded state as pictured in FIG. 3. In an embodiment, the radially expanding debridement tool is instead configured to expand in response to user intervention, such as by pressing a button, axial motion of an interior or exterior shaft, or rotation of an interior or exterior shaft. In an embodiment, a cutting wire is formed from a metal alloy capable of possessing shape memory. In an embodiment, a cutting wire is formed from an alloy of nickel and titanium.

In an embodiment, when the cutting wires are in the unconstrained (expanded) position the distance from the centerline to the tip of at least one of the cutting wires is greater than the width of the shaft. In an embodiment, when the cutting wires are in the unconstrained position the distance from the centerline of the shaft to the tips of the at least two cutting wires is greater than the 75% of the width of the shaft. In an embodiment, when the cutting wires are in the unconstrained position the distance from the centerline of the shaft to the tips of the at least two cutting wires is greater than the width of the shaft. In an embodiment, when the cutting wires are in the unconstrained position the distance from the centerline of the shaft to the tip is different for each of the at least two cutting wires.

As pictured in FIG. 3, the cutting wires have their origin at the same axial location on the shaft. However, the cutting wires have their origin at different radial locations on the shaft. In the expanded state pictured in FIG. 3, the tip of each cutting wires is at a different axial position with respect to the shaft and a different radial distance with respect to the centerline of the shaft. As depicted in FIG. 3, the more distal cutting wire expands radially less than the more proximal cutting wire.

When the radially expanding debridement tool shown in FIG. 3 is in its collapsed state, for instance if it is passing through a narrow access channel in cortical tissue, a guide tube, a cannula, or a carrier tube, the cutting wires will be constrained such that the radially expanding debridement tool will have a width not much greater than the shaft. In an embodiment, when the cutting wires are constrained the radially expanding debridement tool has a width that is not more than 120% of the width of the shaft. In an embodiment, when the cutting wires are constrained in a first position the radially expanding debridement tool has a width that is not more than 110% of the width of the shaft. In an embodiment, when the cutting wires are constrained in a first position the radially expanding debridement tool has a width that is not more than the width of the shaft.

Figure 4:
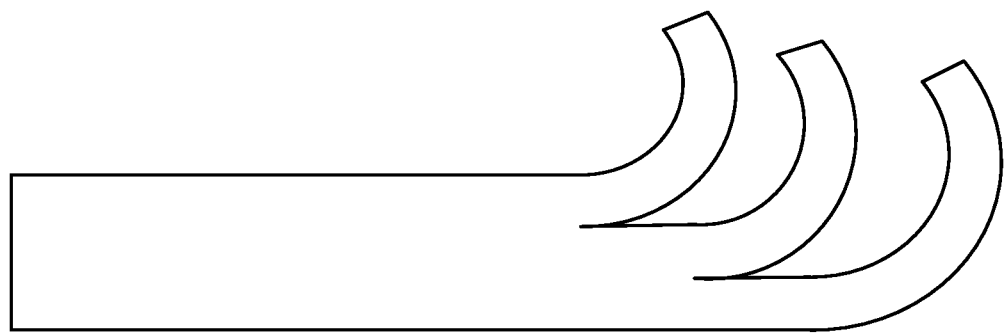
FIG. 4 depicts an embodiment of a radially expanding debridement tool.

FIG. 4 depicts another embodiment of a radially expanding debridement tool. As pictured in FIG. 4, each of the three cutting wires has an origin points at a different axial location on the shaft and a different radial location on the shaft. In the expanded state pictured in FIG. 4, the tip of each cutting wires is at a different axial position with respect to the shaft and a different radial distance with respect to the centerline of the shaft. As depicted in FIG. 4, the distance from the centerline of the shaft to the tip of the cutting wire is least for the most distal cutting wire and greatest for the most proximal cutting wire.

FIG. 5 shows a debridement system. In FIG. 5A the radially expanding debridement tool 51 is position in a carrier tube 50. The radially expanding debridement tool comprises three cutting wires and a knob 56 at its proximal end. In an embodiment, the length of the radially expanding debridement tool is greater than that of the carrier tube.

When positioned in the carrier tube in FIG. 5A the radially expanding debridement tool is in the collapsed position such that the cutting wires are held close to the shaft to allow the tool to pass through the access channel with a narrow profile. In FIG. 5B the debridement system is advanced toward a guide tube 52 positioned in an access channel (not pictured). In FIG. 5C, the radially expanding debridement tool has been advanced through the carrier tube 50 and further into the access channel such that at least one of the cutting wires have exited the carrier tube and assumed the expanded position due to their shape memory. In an embodiment, the carrier tube constrains the radially expanding debridement tool such that the radially expanding debridement tool expands automatically upon being advanced distally past the end of the carrier tube. In such embodiments, the depth to which the carrier tube is advanced distally thereby controls the location at which the radially expanding debridement tool expands.

In an embodiment, in the expanded position the distance from the centerline of the carrier tube to the tip of at least one of the cutting wires is greater than the inner diameter of the carrier tube. In an embodiment, in the expanded position the distance from the centerline of the carrier tube to the tip of at least two of the cutting wires is greater than the inner diameter of the carrier tube. In an embodiment, the distance from the centerline of the carrier tube to the tip is different for each of the at least two cutting wires.

The debridement system may be inserted through an access channel, typically created using a drill bit or trocar. In the case of a trocar, the obturator (spear tip) is removed and the cannula or guide tube left in place to facilitate easy insertion of the carrier tube. Alternatively, once the access channel is formed, a guide tube or cannula may be positioned in the access channel and the debridement system inserted through the guide tube or cannula. When a guide tube or cannula is available, it is possible to use the radially expanding debridement tool without a carrier tube. However, it may be preferred to have it housed within the carrier tube to avoid the creation of debris as the tips scrape along the interior of the guide tube prior to exiting the guide tube.

In the embodiment depicted in FIG. 5, the carrier tube further comprises a flange. The flange is present at one end of the carrier tube, which is the proximal end in operation of the debridement system. The flange serves to stop the carrier tube from being inserted too far into the access channel or guide tube. Furthermore, the flange may fix the location at which the radially expanding debridement tool can expand into the second tissue by controlling a maximum distance to which the carrier tube can be advanced distally. In an embodiment, one or more washers may be added around the carrier tube to effectively thicken the flange and affect the depth from the flange to the proximal end of the access channel or guide tube.

The void is created by rotating, and optionally advancing distally, the radially expanding debridement tool after it has entered its expanded state. After forming the void, the void is likely filled with a fluidized matrix of disrupted tissue. In an embodiment, the fluidized matrix is aspirated from the void. The void can be left open to fill with blood from the surrounding tissue or filled with a at least one support matrix. In an embodiment, the fluidized matrix is displaced by addition of a support matrix.

In an embodiment, at least one support matrix is placed in the void. In an embodiment, the support matrix comprises a bone graft material. In an embodiment, the support matrix comprises an autograft, allograft, xenograft, or a synthetic bone graft substitute. In an embodiment, the synthetic bone graft substitute is a settable calcium phosphate cement, polymer particulate, polymer putty, or settable polymer.

In an embodiment, the support matrix comprises a bioactive agent. In an embodiment, the bioactive agent comprises an angiogenic agent, an anti-bacterial agent, an antibiotic, an anti-fungal, an anti-inflammatory agent, an antioxidant, blood, a blood fraction, bone marrow aspirate, bone marrow aspirate concentrate, cells, a cellular concentrate, a drug, glycosaminoglycans, glycoproteins, a growth factor, a hormone, lipids, morphogens, nucleotides, a painkiller, a peptide, a protein, a radioactive material, a steroid, a surfactant, a vitamin, yeast, or a combination thereof.

In an embodiment, the support matrix comprises a suture mass, suture anchor, or screw. FIG. 6 depicts the placement of a solid suture anchor in the void. FIG. 7 depicts the placement of a flexible or expanding suture anchor in the void. The flexible suture anchor may be a thick suture braid that is pulled into shape by a thin suture braid. Additional guide or placement tools may be used.

In an embodiment, a first support matrix is placed into the void, wherein the first support matrix comprises a suture mass, suture anchor, or screw, and then a second support matrix is placed in the void, wherein the second support matrix is a bone graft material.

Additional Description of Exemplary Embodiments

1. A radially expanding debridement tool configured to pass through an access channel present in a first tissue of a living being, expand radially, and create a void in a second tissue of the living being upon being advanced distally through the access channel and into the second tissue while being rotated, wherein the shape of the void comprises at least one step from a first void section to a second void section, wherein the first void section is more distal than the second void section, and wherein the first void section comprises a maximum radial cross-sectional area that is less than the maximum radial cross-sectional area of the second void section.

2. The radially expanding debridement tool according to any one of the previous embodiments, wherein the first tissue is cortical tissue.

3. The radially expanding debridement tool according to any one of the previous embodiments, wherein the first tissue is cortical bone and the second tissue is cancellous bone.

4. The radially expanding debridement tool according to any one of the previous embodiments, wherein the radially expanding debridement tool comprises a shaft and at least two cutting wires extending from the shaft.

5. The radially expanding debridement tool according to any one of the previous embodiments, wherein the radially expanding debridement tool comprises a shaft and at least two cutting wires extending from the shaft, each of the at least two cutting wires comprising a tip and a cutting edge.

6. The radially expanding debridement tool according to any one of the previous embodiments, wherein the radially expanding debridement tool comprises a shaft and at least two cutting wires extending from the shaft, each of the at least two cutting wires comprising a tip and a cutting edge, and least one of the at least two cutting wires comprising shape memory.

7. The radially expanding debridement tool according to any one of the previous embodiments, wherein the radially expanding debridement tool comprises a shaft and at least two cutting wires extending from the shaft, the at least two cutting wires comprising shape memory, a tip, and a cutting edge.

8. The radially expanding debridement tool according to any one of the previous embodiments, wherein the radially expanding debridement tool is configured to expand automatically.

9. The radially expanding debridement tool according to any one of the previous embodiments, wherein the radially expanding debridement tool is configured to expand in response to user intervention.

10. The radially expanding debridement tool according to any one of the previous embodiments, wherein the radially expanding debridement tool comprises two, three, four, or five cutting wires.

11. The radially expanding debridement tool according to any one of the previous embodiments, wherein the tips of the at least two cutting wires comprise a cutting edge.

12. The radially expanding debridement tool according to any one of the previous embodiments, wherein the at least two cutting wires further comprise at least one cutting edge along at least a portion of their length.

13. The radially expanding debridement tool according to any one of the previous embodiments, wherein the at least two cutting wires further comprise two, three, four, five, or six cutting edges along at least a portion of their length.

14. The radially expanding debridement tool according to any one of the previous embodiments, wherein the at least two cutting wires comprise a cutting edge along their entire length.

15. The radially expanding debridement tool according to any one of the previous embodiments, wherein the at least two cutting wires comprise a polygonal cross-section.

16. The radially expanding debridement tool according to any one of the previous embodiments, wherein the at least two cutting wires comprise a triangular cross-section.

17. The radially expanding debridement tool according to any one of the previous embodiments, wherein the at least two cutting wires comprise a square cross-section.

18. The radially expanding debridement tool according to any one of the previous embodiments, wherein the at least two cutting wires comprise a rectangular cross-section.

19. The radially expanding debridement tool according to any one of the previous embodiments, wherein the at least two cutting wires comprise a circular cross-section.

20. The radially expanding debridement tool according to any one of the previous embodiments, wherein one or more of the cutting wires comprise a plurality of tips.

21. The radially expanding debridement tool according to any one of the previous embodiments, wherein the shaft has a circular cross-section.

22. The radially expanding debridement tool according to any one of the previous embodiments, wherein the shaft has a rectangular cross-section.

23. The radially expanding debridement tool according to any one of the previous embodiments, wherein the portion of each cutting wire that will enter the body is attached as a single unit to the portion of the each cutting wire that will remain outside the body.

24. The radially expanding debridement tool according to any one of the previous embodiments, wherein the cutting wires form at least part of the shaft.

25. The radially expanding debridement tool according to any one of the previous embodiments, wherein an origin point of each of the at least two cutting wires has a different axial location on the shaft.

26. The radially expanding debridement tool according to any one of the previous embodiments, wherein an origin point of each of the at least two cutting wires has a different radial distance from the centerline of the shaft.

27. The radially expanding debridement tool according to any one of the previous embodiments, wherein an origin point of each of the at least two cutting wires has a different radial distance from the centerline of the shaft and a different axial location on the shaft.

28. The radially expanding debridement tool according to any one of the previous embodiments, wherein the positions of the tips of the at least two cutting wires, when expanded, are at different radial distances with respect to the centerline of the shaft.

29. The radially expanding debridement tool according to any one of the previous embodiments, wherein the positions of the tips of the at least two cutting wires are at different axial positions with respect to the shaft.

30. The radially expanding debridement tool according to any one of the previous embodiments, wherein the positions of the tips of the at least two cutting wires, when expanded, are at different radial distances with respect to the centerline of the shaft and at different axial positions with respect to the shaft.

31. The radially expanding debridement tool according to any one of the previous embodiments, wherein the tip of a first cutting wire has a smaller radial distance with respect to the centerline of the shaft than a second, more proximal cutting wire when the at least two cutting wires are expanded.

32. The radially expanding debridement tool according to any one of the previous embodiments, wherein the tip of a second cutting wire has a greater radial distance with respect to the centerline of the shaft than a first, more distal cutting wire when the at least two cutting wires are expanded.
33. The radially expanding debridement tool according to any one of the previous embodiments, wherein the tip of any cutting wire has a greater radial distance with respect to the centerline of the shaft than any more distal cutting wire when the at least two cutting wires are expanded.
34. The radially expanding debridement tool according to any one of the previous embodiments, wherein the tip of any cutting wire has a smaller radial distance with respect to the centerline of the shaft than any more proximal cutting wire when the at least two cutting wires are expanded.
35. The radially expanding debridement tool according to any one of the previous embodiments, wherein the tip of the most distal cutting wire has the smallest radial distance with respect to the centerline of the shaft relative to any of the other tips of the at least two cutting wires when the at least two cutting wires are expanded.
36. The radially expanding debridement tool according to any one of the previous embodiments, wherein the tip of the most proximal cutting wire has the greatest radial distance with respect to the centerline of the shaft relative to any of the other tips of the at least two cutting wires when the at least two cutting wires are expanded.
37. The radially expanding debridement tool according to any one of the previous embodiments, wherein a more distal cutting wire expands radially less than a more proximal cutting wire.
38. The radially expanding debridement tool according to any one of the previous embodiments, wherein a more proximal cutting wire expands radially more than a more distal cutting wire.
39. The radially expanding debridement tool according to any one of the previous embodiments, wherein each cutting wire expands radially less than any cutting wire that is more proximal.
40. The radially expanding debridement tool according to any one of the previous embodiments, wherein each cutting wire expands radially more than any cutting wire that is more distal.
41. The radially expanding debridement tool according to any one of the previous embodiments, wherein the most distal cutting wire expands radially less than any other cutting wire.
42. The radially expanding debridement tool according to any one of the previous embodiments, wherein the most proximal cutting wire expands radially more than any other cutting wire.
43. The radially expanding debridement tool according to any one of the previous embodiments, wherein when the cutting wires are constrained in a first position the radially expanding debridement tool has a width that is not more than 120% of the width of the shaft.
44. The radially expanding debridement tool according to any one of the previous embodiments, wherein when the cutting wires are constrained in a first position the radially expanding debridement tool has a width that is not more than 110% of the width of the shaft.
45. The radially expanding debridement tool according to any one of the previous embodiments, wherein when the cutting wires are constrained in a first position the radially expanding debridement tool has a width that is not more than the width of the shaft.
46. The radially expanding debridement tool according to any one of the previous embodiments, wherein when the cutting wires are in a second, unconstrained position the distance from the centerline to the tip of at least one of the cutting wires is greater than 75% of the width of the shaft.
47. The radially expanding debridement tool according to any one of the previous embodiments, wherein when the cutting wires are in a second, unconstrained position the distance from the centerline to the tip of at least one of the cutting wires is greater than the width of the shaft.
48. The radially expanding debridement tool according to any one of the previous embodiments, wherein when the cutting wires are in a second, unconstrained position the distance from the centerline to the tips of the at least two cutting wires is greater than the width of the shaft.
49. The radially expanding debridement tool according to any one of the previous embodiments, wherein when the cutting wires are in a second, unconstrained position the distance from the centerline to the tip is different for each of the at least two cutting wires.
50. The radially expanding debridement tool according to any one of the previous embodiments, wherein the tool comprises a metal alloy possessing shape memory.
51. The radially expanding debridement tool according to any one of the previous embodiments, wherein the tool comprises an alloy of nickel and titanium.
52. The radially expanding debridement tool according to any one of the previous embodiments, wherein a cutting wire is formed from a metal alloy capable of possessing shape memory.
53. The radially expanding debridement tool according to any one of the previous embodiments, wherein a cutting wire is formed from an alloy of nickel and titanium.
54. The radially expanding debridement tool according to any one of the previous embodiments, wherein a first void section is the portion of the void that is present from the void's most distal point to the first step.
55. The radially expanding debridement tool according to any one of the previous embodiments, wherein the void comprises two steps and the first void section is the portion of the void that is present from the void's most distal point to the more distal step, the second void section is the portion of the void from the first step to the more proximal step, and the third void section is the remainder of the void.
56. The radially expanding debridement tool according to any one of the previous embodiments, wherein the maximum radial cross-sectional area for a given void section is the largest area of the void section in any of the planes that are perpendicular to the axis of rotation of the radially expanding debridement tool after one full rotation of the radially expanding debridement tool.
57. The radially expanding debridement tool according to any one of the previous embodiments, wherein the void comprises at least one step, at least two steps, or at least three steps.
58. The radially expanding debridement tool according to any one of the previous embodiments, wherein the void comprises at least two void sections, at least three void sections, or at least four void sections.
59. The radially expanding debridement tool according to any one of the previous embodiments, wherein a void comprises a first void section and a second void section.
60. The radially expanding debridement tool according to any one of the previous embodiments, wherein a void comprises a first void section, a second void section, and a third void section.
61. The radially expanding debridement tool according to any one of the previous embodiments, wherein a void comprises a first void section, a second void section, a third void section, and a fourth void section.

62. The radially expanding debridement tool according to any one of the previous embodiments, wherein the void section with the greatest maximum radial cross-sectional area is the most proximal void section.

63. The radially expanding debridement tool according to any one of the previous embodiments, wherein the void section with the smallest maximum radial cross-sectional area is the most distal void section.

64. The radially expanding debridement tool according to any one of the previous embodiments, wherein a void comprises a first void section and a second void section, and wherein a second void section has a maximum radial cross-sectional area that is at least 1.05 times, at least 1.1 times, at least 1.2 times, at least 1.3 times, at least 1.4 times, at least 1.5 times, at least 1.6 times, at least 1.7 times, at least 1.8 times, at least 1.9 times, at least 2 times, at least 2.1 times, at least 2.2 times, at least 2.3 times, at least 2.4 times, or at least 2.5 times the maximum radial cross-sectional area of the first void section, wherein the first void section is more distal than the second void section.

65. The radially expanding debridement tool according to any one of the previous embodiments, wherein a second void section has a maximum radial cross-sectional area that is at most 10 times, at most 9 times, at most 8 times, at most 7 times, at most 6 times, at most 5 times, at most 4 times, at most 3 times, at most 2.5 times, at most 2 times, or at most 1.5 times the maximum radial cross-sectional area of the first void section, wherein the first void section is more distal than the second void section.

66. The radially expanding debridement tool according to any one of the previous embodiments, wherein a third void section has a maximum radial cross-sectional area that is at least 1.05 times, at least 1.1 times, at least 1.2 times, at least 1.3 times, at least 1.4 times, at least 1.5 times, at least 1.6 times, at least 1.7 times, at least 1.8 times, at least 1.9 times, at least 2 times, at least 2.1 times, at least 2.2 times, at least 2.3 times, at least 2.4 times, or at least 2.5 times the maximum radial cross-sectional area of the second void section, wherein the second void section is more distal than the third void section.

67. The radially expanding debridement tool according to any one of the previous embodiments, wherein a third void section has a maximum radial cross-sectional area that is at most 10 times, at most 9 times, at most 8 times, at most 7 times, at most 6 times, at most 5 times, at most 4 times, at most 3 times, at most 2.5 times, at most 2 times, or at most 1.5 times the maximum radial cross-sectional area of the second void section, wherein the second void section is more distal than the third void section.

68. The radially expanding debridement tool according to any one of the previous embodiments, wherein a fourth void section has a maximum radial cross-sectional area that is at least 1.05 times, at least 1.1 times, at least 1.2 times, at least 1.3 times, at least 1.4 times, at least 1.5 times, at least 1.6 times, at least 1.7 times, at least 1.8 times, at least 1.9 times, at least 2 times, at least 2.1 times, at least 2.2 times, at least 2.3 times, at least 2.4 times, or at least 2.5 times the maximum radial cross-sectional area of the third void section, wherein the third void section is more distal than the fourth void section.

69. The radially expanding debridement tool according to any one of the previous embodiments, wherein a fourth void section has a maximum radial cross-sectional area that is at most 10 times, at most 9 times, at most 8 times, at most 7 times, at most 6 times, at most 5 times, at most 4 times, at most 3 times, at most 2.5 times, at most 2 times, or at most 1.5 times the maximum radial cross-sectional area of the third void section, wherein the third void section is more distal than the fourth void section.

70. A debridement system comprising:
    a. a carrier tube having an inner diameter, a proximal end, a distal end, and a centerline,
    b. a radially expanding debridement tool of any one of the preceding embodiments positioned in the carrier tube.

71. The debridement system according to the previous embodiment, wherein the cutting wires are constrained in the carrier tube at a first position, and wherein when the radially expanding debridement tool is advanced distally through the carrier tube the cutting wires exit the carrier tube and at least one of the cutting wires assumes a second position due to its shape memory and wherein the distance from the centerline to the tip of at least one of the at least two cutting wires is greater than the inner diameter of the carrier tube.

72. The debridement system according to any one of the previous embodiments, wherein the carrier tube further comprises a flange.

73. The debridement system according to any one of the previous embodiments, wherein the flange is configured to fix the location at which the radially expanding debridement tool can expand into the second tissue by controlling a maximum distance to which the carrier tube can be advanced distally.

74. The debridement system according to any one of the previous embodiments, further comprising a removable washer around the carrier tube.

75. The debridement system according to any one of the previous embodiments, further comprising a removable washer, wherein the washer is configured to be placed around the carrier tube proximate the flange and thereby affect the depth to which the carrier tube may be inserted into the access channel.

76. The debridement system according to any one of the previous embodiments, wherein the cutting wires are constrained in the carrier tube at a first position, and wherein when the radially expanding debridement tool is advanced distally through the carrier tube the cutting wires exit the carrier tube and assume a second position due to their shape memory and wherein the distance from the centerline to the tip of each of the at least two cutting wires is greater than the diameter of the carrier tube.

77. The debridement system according to any one of the previous embodiments, wherein the distance from the centerline of the carrier tube to the tip is different for each of the at least two cutting wires.

78. A method of treating a tissue defect in a living being, comprising the steps of:
    a. creating an access channel through a region of cortical bone, the access channel possessing a centerline,
    b. inserting in the access channel the radially expanding debridement tool or radially expanding debridement system of any one of the previous embodiments,
    c. advancing the radially expanding debridement tool distally through the access channel, causing the at least two cutting wires to expand upon leaving the access channel and entering a region of cancellous bone,
    d. rotating the radially expanding debridement tool, thereby creating a void in the cancellous bone, wherein the void comprises a diameter greater than the diameter of the access channel.

79. The method of any one of the preceding embodiments, wherein upon being advanced distally beyond the access channel and into cancellous bone the wires expand due to their shape memory such that the distance from the centerline to the tip of at least one of the at least two cutting wires is greater than the radius of the access channel.

80. The method of any one of the preceding embodiments, wherein upon being advanced distally beyond the access channel and into cancellous bone the wires expand due to their shape memory such that the distance from the centerline to the tip of a plurality of the at least two cutting wires is greater than the radius of the access channel.

81. The method of any one of the preceding embodiments, wherein the void comprises a fluidized matrix.

82. The method of any one of the preceding embodiments, further comprising the step of at least partially removing the fluidized matrix from the void.

83. The method of any one of the preceding embodiments, further comprising the step of retracting the radially expanding debridement tool through the access channel.

84. The method of any one of the preceding embodiments, further comprising the step of placing at least one support matrix into the void.

85. The method of any one of the preceding embodiments, further comprising the step of aspirating the void prior to placing any support matrix into the void.

86. The method of any one of the preceding embodiments, wherein the support matrix comprises a bone graft material.

87. The method of any one of the preceding embodiments, wherein the support matrix comprises an autograft, allograft, xenograft, synthetic bone graft substitute, polymer particulate, polymer putty, or settable polymer.

88. The method of any one of the preceding embodiments, wherein the support matrix comprises a suture mass, suture anchor, or screw.

89. The method of any one of the preceding embodiments, further comprising the steps of placing a first support matrix into the void, wherein the first support matrix comprises a suture mass, suture anchor, or screw, and placing a second support matrix into the void, wherein the second support matrix comprises a bone graft material.

90. The tool, system, or method according to any one of the previous embodiments, wherein the void comprises a minimum width at the most distal end of the void and a greater width at the portion of the void that is nearest the access channel.

91. The tool, system, or method according to any one of the previous embodiments, wherein the void comprises the shape of a plurality of concentric cylinders abutting one another.

92. The tool, system, or method according to any one of the previous embodiments, wherein the void comprises the shape of at least two cylinders of different diameters, wherein a surface of a first cylinder of the at least two cylinders abuts the surface of a second cylinder of the at least two cylinders.

93. The tool, system, or method according to any one of the previous embodiments, wherein the at least two cylinders are coaxial.

94. The tool, system, or method according to any one of the previous embodiments, wherein the at least two cylinders are not coaxial.

95. The tool, system, or method according to any one of the previous embodiments, wherein the void comprises the shape of at least three cylinders of different diameters, wherein a surface of a first cylinder of the at least three cylinders abuts the surface of a second cylinder of the at least three cylinders.

96. The tool, system, or method according to any one of the preceding embodiments, wherein the void comprises at least two steps of varying diameter.

97. The tool, system, or method according to any one of the preceding embodiments, wherein the void comprises from two to five steps of varying diameter.

98. The tool, system, or method according to any one of the preceding embodiments, wherein the void comprises a taper extending from the access channel to the void's maximum width.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. While certain optional features are described as embodiments of the invention, the description is meant to encompass and specifically disclose all combinations of these embodiments unless specifically indicated otherwise or physically impossible.

The invention claimed is:

1. A radially expanding debridement tool comprising:
a radially expanding portion configured to pass through an access channel present in a first tissue of a living being, expand radially, and create a void in a second tissue of the living being upon being advanced distally through the access channel and into the second tissue while being rotated,
wherein a shape of the void comprises at least two steps,
wherein a first step is present from a first void section to a second void section, wherein the first void section is more distal than the second void section, and wherein the first void section comprises a maximum radial cross-sectional area that is less than a maximum radial cross-sectional area of the second void section, and
wherein a second step is present from the second void section to a third void section, wherein the second void section is more distal than the third void section, and wherein the maximum radial cross-sectional area of the second void section is less than a maximum radial cross-sectional area of the third void section.

2. The radially expanding debridement tool according to claim 1, wherein the first tissue is cortical bone and the second tissue is cancellous bone.

3. The radially expanding debridement tool according to claim 1, wherein the radially expanding debridement tool comprises a shaft and at least two cutting wires extending from the shaft, the at least two cutting wires each comprising shape memory, a tip, and a cutting edge.

4. The radially expanding debridement tool according to claim 3, wherein the tip of each of the at least two cutting wires comprise a cutting edge and wherein each of the at least two cutting wires further comprise at least one cutting edge along at least a portion of their length.

5. The radially expanding debridement tool according to claim 3, wherein the at least two cutting wires comprise a polygonal cross-section.

6. The radially expanding debridement tool according to claim 3, wherein the cutting wires form at least part of the shaft.

7. The radially expanding debridement tool according to claim 3, wherein an origin point of each of the at least two cutting wires has a different radial distance from a centerline of the shaft and a different axial location on the shaft.

8. The radially expanding debridement tool according to claim 3, wherein, when expanded, a tip of a first cutting wire is at a different radial distance with respect to a centerline of the shaft and at a different axial position with respect to the shaft than a tip of a second cutting wire.

9. The radially expanding debridement tool according to claim 3, wherein the tip of a first cutting wire has a smaller radial distance with respect to a centerline of the shaft than a second, more proximal cutting wire when the at least two cutting wires are expanded.

10. The radially expanding debridement tool according to claim 3, wherein the tip of any cutting wire has a smaller radial distance with respect to a centerline of the shaft than any more proximal cutting wire when the at least two cutting wires are expanded.

11. The radially expanding debridement tool according to claim 3, wherein each cutting wire expands radially less than any cutting wire that is more proximal.

12. The radially expanding debridement tool according to claim 1, wherein the void comprises a maximum of two steps and the first void section is a portion of the void that is present from the void's most distal point to a most distal step, the second void section is a portion of the void from the first step to a second most distal step, and a third void section is a remainder of the void.

13. The radially expanding debridement tool according to claim 1, wherein a most proximal void section has a greater maximum radial cross-section area than any other void section.

14. The radially expanding debridement tool according to claim 13, wherein a most distal void section has a smaller maximum radial cross-sectional area than any other void section.

15. The radially expanding debridement tool according to claim 1, wherein the maximum radial cross-sectional area of the second void section is at least 1.2 times and at most 3 times the maximum radial cross-sectional area of the first void section.

16. The radially expanding debridement tool according to claim 15, wherein the maximum radial cross-sectional area of the third void section is at least 1.2 times and at most 3 times the maximum radial cross-sectional area of the second void section.

17. The radially expanding debridement tool according to claim 1, wherein the void comprises a taper extending from the access channel to the void's maximum width.

* * * * *